(12) United States Patent
Li

(10) Patent No.: US 11,291,778 B2
(45) Date of Patent: Apr. 5, 2022

(54) LIQUID CONSTANT TEMPERATURE HEATING APPARATUS, INFUSION DEVICE AND FORMULA MILK PREPARATION DEVICE

(71) Applicant: BOE TECHNOLOGY GROUP CO., LTD., Beijing (CN)

(72) Inventor: Zhenglong Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 737 days.

(21) Appl. No.: 16/099,034

(22) PCT Filed: Apr. 27, 2018

(86) PCT No.: PCT/CN2018/084848
§ 371 (c)(1),
(2) Date: Nov. 5, 2018

(87) PCT Pub. No.: WO2019/019740
PCT Pub. Date: Jan. 31, 2019

(65) Prior Publication Data
US 2021/0220572 A1 Jul. 22, 2021

(30) Foreign Application Priority Data
Jul. 24, 2017 (CN) .......................... 201710607279.3

(51) Int. Cl.
*A61M 5/44* (2006.01)
*A61M 5/168* (2006.01)
*F24H 9/00* (2022.01)
*G05B 11/42* (2006.01)
*G05B 13/02* (2006.01)
*G05D 23/19* (2006.01)
*G06N 3/04* (2006.01)

(52) U.S. Cl.
CPC ........ *A61M 5/445* (2013.01); *A61M 5/16881* (2013.01); *F24H 9/0015* (2013.01);
(Continued)

(58) Field of Classification Search
CPC ...... A47J 31/4485; A47J 31/56; A47J 31/542; A47J 31/401; A47J 31/40; A47J 31/00; A47J 31/60; A47J 31/46; A47J 31/4489; A47J 31/54; A47J 31/545; A61M 5/44
See application file for complete search history.

(56) References Cited

U.S. PATENT DOCUMENTS 4,966,579 A * 10/1990 Polaschegg ....... A61M 5/16831
604/65
5,125,069 A 6/1992 O'Boyle
(Continued)

FOREIGN PATENT DOCUMENTS

| CN | 1965743 A | 5/2007 |
| CN | 2917668 Y * | 7/2007 |

(Continued)

OTHER PUBLICATIONS

CN2917668 translation. (Year: 2007).*
(Continued)

*Primary Examiner* — Manuel A Mendez

(57) ABSTRACT

The present disclosure provides a liquid constant temperature heating apparatus, an infusion device and a formula milk preparation device. The liquid constant temperature heating apparatus includes: a heating portion, the heating portion having a heating chamber, and the heating chamber having a liquid inlet and a liquid outlet; a liquid inlet pipe, the liquid inlet pipe being connected with the liquid inlet of the heating portion; a liquid outlet pipe, the liquid outlet pipe being connected with the liquid outlet of the heating portion; a temperature sensor, the temperature sensor being arranged on the liquid outlet pipe and in communication with the heating portion; and a controller, which is in signal connection with the temperature sensor by a signal and configured to control heating of the heating portion according to a measurement result of the temperature sensor.

18 Claims, 2 Drawing Sheets

(52) U.S. Cl.
CPC ............ *G05B 11/42* (2013.01); *G05B 13/027* (2013.01); *G05D 23/1919* (2013.01); *G05D 23/1928* (2013.01); *G06N 3/0445* (2013.01); *A61M 2205/3368* (2013.01); *A61M 2205/366* (2013.01); *A61M 2205/502* (2013.01); *A61M 2205/52* (2013.01); *A61M 2205/581* (2013.01); *A61M 2205/587* (2013.01)

(56) References Cited

U.S. PATENT DOCUMENTS

| | | | | |
|---|---|---|---|---|
| 5,793,022 | A | * | 8/1998 | Klinck ................ G05B 13/024 219/483 |
| 6,118,933 | A | | 9/2000 | Roberson |
| 7,757,600 | B2 | * | 7/2010 | Jones .................... A47J 31/402 99/275 |
| 2017/0173262 | A1 | * | 6/2017 | Veltz .................... A61B 5/0022 |

FOREIGN PATENT DOCUMENTS

| | | | |
|---|---|---|---|
| CN | 29176668 | Y | 7/2007 |
| CN | 202143737 | U | 2/2012 |
| CN | 202134737 | U | 5/2012 |
| CN | 202361651 | U * | 8/2012 |
| CN | 202361651 | U | 8/2012 |
| CN | 206094524 | U | 4/2017 |
| CN | 206176750 | U | 5/2017 |
| CN | 106820989 | A | 6/2017 |

OTHER PUBLICATIONS

CN202361651 translation (Year: 2012).*
The International Search Report and Written Opinion dated May 29, 2018; PCT/CN2018/084848.
The First Chinese Office Action dated Jun. 12, 2019; Appln. No. 201710607279.3.

* cited by examiner

LIQUID CONSTANT TEMPERATURE HEATING APPARATUS, INFUSION DEVICE AND FORMULA MILK PREPARATION DEVICE

TECHNICAL FIELD

Embodiments of the present disclosure relate to a liquid constant temperature heating apparatus, an infusion device with the liquid constant temperature heating apparatus and a formula milk preparation device with the liquid constant temperature heating apparatus.

BACKGROUND

In a medical system, liquid supplementation to patients or special groups is one kind of conventional treatment means. Methods for supplementing liquid include direct intravenous infusion, oral administration of liquid, and the like. Generally, for liquid supplementation, such as solvents of normal saline, glucose, and the like, the storage condition is the room temperature. When a patient is subjected to intravenous infusion, the stored liquid is generally directly infused into the human body by a syringe. On cold days, when the patient receives a great amount of injection, of which a temperature is lower than the body temperature, the patient will feel uncomfortable and even the condition of the patient will be affected.

In the Neonatal Intensive Care Unit (NICU), in order to avoid infection, generally, parents are forbidden from entering. Newborns are generally fed by feeding bottles, and generally, formula milk powder is prepared into milk liquid by utilizing warm water. There are strict requirements on the temperature of the milk liquid, and generally, it is required that the temperature of the prepared liquid milk is in vicinity of the temperature of the human body: 38 to 40 DEG C. Specifically, cold water is first injected into the milk bottle, then hot water is added, and after the water temperature is tested, the formula milk powder is added. Such mode is very difficult to rapidly and instantaneously prepare a great amount of milk powder, particularly when the manual operation is carried out.

SUMMARY

Embodiments of the present disclosure provide a liquid constant temperature heating apparatus, an infusion device and a formula milk preparation device.

In a first aspect, an embodiment of the present disclosure provides a liquid constant temperature heating apparatus, comprising: a heating portion, the heating portion having a heating chamber, and the heating chamber having a liquid inlet and a liquid outlet; a liquid inlet pipe, the liquid inlet pipe being connected with the liquid inlet of the heating portion; a liquid outlet pipe, the liquid outlet pipe being connected with the liquid outlet of the heating portion; a temperature sensor, the temperature sensor being arranged on the liquid outlet pipe and in communication with the heating portion; and a controller, which is in signal connection with the temperature sensor by a signal and configured to control heating of the heating portion according to a measurement result of the temperature sensor.

For example, the liquid constant temperature heating apparatus further comprises: a buffer, the buffer being arranged on the liquid outlet pipe.

For example, the liquid constant temperature heating apparatus further comprises: a flow restriction valve, the flow restriction valve being arranged on the liquid inlet pipe.

For example, the flow restriction valve is positioned between a check valve and the liquid inlet of the heating portion in a length direction of the liquid inlet pipe.

For example, the buffer is a telescopic pipe, the liquid outlet pipe has a gap, and both ends of the telescopic pipe are respectively connected with both ends of the gap of the liquid outlet pipe.

For example, a length of the telescopic pipe along a liquid flowing direction is greater than a distance between both ends of the gap of the liquid outlet pipe.

For example, the check valve is positioned at the upstream of the heating portion along the liquid flowing direction.

For example, the temperature sensor is positioned at the downstream of the heating portion along the liquid flowing direction.

For example, the liquid inlet and the liquid outlet are respectively positioned at both ends of the longest liquid path of the heating portion.

For example, the liquid constant temperature heating apparatus further comprises: a check valve, the check valve being arranged on the liquid inlet pipe and unidirectionally conducted along a direction of the liquid inlet pipe, which faces the liquid inlet.

For example, the controller is a Proportional-Integral-Derivative controller and is configured to acquire a temperature measurement time sequence of the temperature sensor and a signal, which corresponds to the time sequence and is input to the heating portion by the controller and generate a control parameter of the Proportional-Integral-Derivative controller by a neural network, and the neural network is a Long Short Term Memory network.

In a second aspect, an embodiment of the present disclosure provides an infusion device, comprising: the liquid constant temperature heating apparatus according to the embodiments in the first aspect of the present disclosure; and a cutoff catheter, the cutoff catheter being connected with the liquid outlet pipe and in communication with the temperature sensor, and the cutoff catheter, in response to a detection result of the temperature sensor, cutting off flowing liquid or keeping the liquid flowing.

In a second aspect, an embodiment of the present disclosure provides a formula milk preparation device, comprising: a storage container; the liquid constant temperature heating apparatus according to the embodiments in the first aspect of the present disclosure, one end of the liquid inlet pipe, which faces away from the heating portion, and one end of the liquid outlet pipe, which faces away from the heating portion, extending into the storage container.

For example, the formula milk preparation device further comprises: an auxiliary temperature sensor, the auxiliary temperature sensor being arranged on the liquid inlet pipe; and a control unit, the control unit being in communication with the temperature sensor and the auxiliary temperature sensor and when a difference between detection values of the temperature sensor and the auxiliary temperature sensor is smaller than a preset threshold, providing information representing that a temperature meets the requirement.

BRIEF DESCRIPTION OF THE DRAWINGS

The above mentioned aspects an disadvantages and/or additional ones become apparent and understandable in connection with the description with reference to the following accompanying drawings.

DETAILED DESCRIPTION

Figure 1:
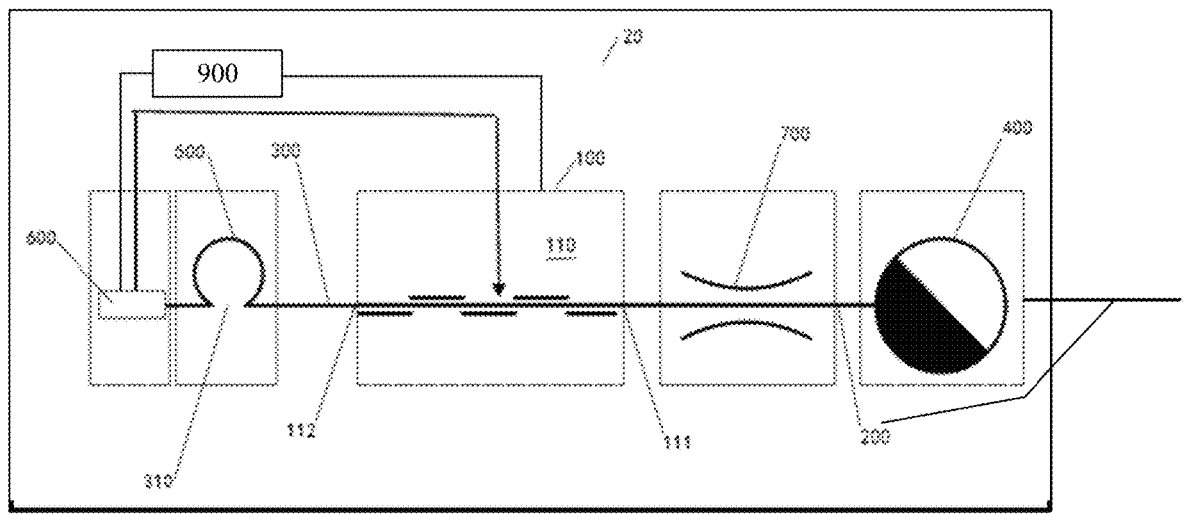
FIG. 1 is a structural schematic diagram of a liquid constant temperature heating apparatus according to an embodiment of the present disclosure.

In the following the embodiments of the present disclosure are described, and the examples of the embodiments are illustrated in the drawings; throughout the drawings the same or similar reference numbers represent the same or similar components or elements having the same or similar functions. The embodiments described with reference to drawings are exemplary and used to explain the present disclosure, but cannot be understood to be limitations to the present disclosure.

In the description to the embodiments of the present disclosure, it should be understood that the direction or position represented by the terms "length" and so on is the direction or position based on the showing of the drawings, they are only for describing the present disclosure and simplifying description, but not for explicitly or implicitly describing that the device or component at issue should have the specified direction and the specified construction or operation, and therefore they cannot be explained to be limitation to the present disclosure.

In the description to the embodiments of the present disclosure, it should be understood that, unless otherwise specified or defined, the terms "amount", "connect", "connected" and so on should be understood in a broad concept, and for example, the components can be fixedly connected or detachably connected, or integratedly connected. For those skilled in the related technical art can understand these terms in a specific context.

A liquid constant temperature heating apparatus 20 according to an embodiment of the present disclosure will be described below with reference to the drawing.

As shown in FIG. 1, a liquid constant temperature heating apparatus 20 according to the embodiments of the present disclosure includes a heating portion 100, a liquid inlet pipe 200, a liquid outlet pipe 300, a check valve 400, a buffer 500 and a temperature sensor 600.

The heating portion 100 has a heating chamber 110, and the heating chamber 110 has a liquid inlet 111 and a liquid outlet 112. The liquid inlet pipe 200 is connected with the liquid inlet 111 of the heating portion 100. The liquid outlet pipe 300 is connected with the liquid outlet 112 of the heating portion 100. A controller 900 is in signal connection with the temperature sensor and configured to control the heating operation of the heating portion according to the measurement result of the temperature sensor. The check valve 400 is arranged on the liquid inlet pipe 200 and unidirectionally conducted along the direction of the liquid inlet pipe 200, which direction faces the liquid inlet 111. The buffer 500 is arranged on the liquid outlet pipe 300. The temperature sensor 600 is arranged on the liquid outlet pipe 300 and in communication with the heating portion 100.

When the liquid constant temperature heating apparatus 20 works, liquid enters from the liquid inlet pipe 200, sequentially passes through the check valve 400, the heating portion 100, the buffer 500 and the temperature sensor 600, and finally, flows out of the liquid outlet pipe 300.

In the present disclosure, the liquid inlet pipe 200 may include a pipeline positioned at the upstream of the check valve 400 to convey liquid to the check valve 400, and include connection pipelines between the check valve 400 and the liquid inlet 111 and between parts, and the embodiments of the present disclosure are not limited in this aspect.

Exemplarily, the controller is a Proportional-Integral-Derivative (PID) controller and is configured to acquire a temperature measurement time sequence of the temperature sensor and a signal, which corresponds to the time sequence and is input to the heating portion by the controller and generate a control parameter of the PID controller by a neural network, and the neural network is a Long Short Term Memory (LSTM). For liquid temperature control of general devices, there are following main problems below: 1) the conduction delay of the temperature of a heater and the liquid temperature at a terminal outlet is relatively large; and 2) when the temperature of the heater is excessively high, it is very easy to cause oscillation of the liquid temperature at the outlet. Generally, fuzzy control is adopted. But the problems with fuzzy control is that fuzzy control rules need to be manually set, which is very dependent on experience of engineers. Meanwhile, for medical liquid, it is absolutely not allowed that the temperature is excessively high by a large amplitude. According to the embodiments of the present disclosure, time information of outlet temperature variations is utilized, and when the temperature rise tendency is excessively fast, prediction can be timely carried out so as to terminate the excessively fast temperature rise; and when the temperature rise is slow, the temperature rise can be effectively accelerated.

The check valve 400 is used for controlling the flowing direction of liquid so as to avoid pollution caused by liquid backflow, and when the liquid constant temperature heating apparatus 20 is used for an infusion device, the check valve 400 can avoid venous return. The heating portion 100 may be a closed cavity, and is used for carrying out heating on the liquid in the heating chamber 110. The buffer 500 is used for preventing the excessively fast temperature rise of the liquid so as to realize a buffer effect. The temperature sensor 600 is used for detecting the temperature of the heated liquid and simultaneously for feeding back the detection result to the heating portion 100 to control heating parameters, such as time, power and the like, so as to implement effective control on a liquid heating temperature, thereby carrying out constant temperature heating.

Therefore, the liquid constant temperature heating apparatus 20 according to the embodiments of the present disclosure can implement constant temperature heating of the liquid so as to supplement the liquid to a patient or prepare the solution with the temperature requirement.

The liquid constant temperature heating apparatus 20 according to specific examples of the present disclosure will be described below with reference to the drawing.

As shown in FIG. 1, the liquid constant temperature heating apparatus 20 according to the embodiments of the present disclosure includes the heating portion 100, the liquid inlet pipe 200, the liquid outlet pipe 300, the check valve 400, the buffer 500 and the temperature sensor 600.

In some specific examples of the present disclosure, as shown in FIG. 1, the liquid constant temperature heating apparatus 20 further includes a flow restriction valve 700, the flow restriction valve 700 is arranged on the liquid inlet pipe 200; and by arranging the flow restriction valve 700, an excessively high flow rate of the liquid in the liquid inlet pipe 200 can be avoided, and the heating portion 100 is guaranteed to sufficiently heat the liquid in the heating chamber 110.

Further, as shown in FIG. 1, the flow restriction valve 700 is positioned between the check valve 400 and the liquid inlet 111 of the heating portion 100 in the length direction of the liquid inlet pipe 200. Therefore, in one aspect, the flow restriction valve 700 is closer to the liquid inlet 111 of the heating portion 100 and can restrict the flow rate of the liquid entering the heating chamber 110 better, and in the other aspect, the backflow prevention effect of the check valve 400 can be further improved.

In some specific examples of the present disclosure, as shown in FIG. 1, the buffer 500 is a telescopic pipe, the liquid outlet pipe 300 has a gap 310, i.e., the gap 310 cuts off the liquid outlet pipe 300 in the length direction of the liquid outlet pipe 300, and both ends of the telescopic pipe (the buffer 500) are respectively connected with both ends of the gap 310 of the liquid outlet pipe 300. In the process of flowing through the liquid outlet pipe 300, the liquid can pass through the telescopic pipe, so that the liquid is buffered and the excessively fast temperature rise of the liquid is avoided.

Further, as shown in FIG. 1, the length of the telescopic pipe (the buffer 500) along the liquid flowing direction is greater than the distance between both ends of the gap 310 of the liquid outlet pipe 300. In other words, the length of the telescopic pipe along the length direction of the telescopic pipe is greater than the length of the gap 310 along the length direction of the liquid outlet pipe 300, and the telescopic pipe may be constructed in a circular arc structure. Therefore, the buffer effect of the telescopic pipe on the liquid can be further improved.

The liquid outlet pipe 300 and the telescopic pipe may be an integrated part, so that an assembling process can be simplified, and the risk of leakage at the joint of the liquid outlet pipe 300 and the telescopic pipe is eliminated.

In some specific examples of the present disclosure, as shown in FIG. 1, the check valve 400 is positioned at one end of the liquid inlet pipe 200, which faces away from the heating portion 100, so as to improve the backflow prevention effect; and the temperature sensor 600 is positioned at one end of the liquid outlet pipe 300, which faces away from the heating portion 100, so as to improve the accuracy of detection of a liquid outlet temperature.

In some specific examples of the present disclosure, as shown in FIG. 1, the liquid inlet 111 and the liquid outlet 112 are respectively positioned on two opposite side walls of the heating portion 100, thereby not only enabling the liquid flowing through the heating chamber 110 to be sufficiently heated, but also facilitating the connection of the liquid inlet pipe 200 with the heating portion 100 and the liquid outlet pipe 300 with the heating portion 100 and avoiding interference between the liquid inlet pipe 200 and the liquid outlet pipe 300.

Alternatively, the liquid inlet 111 and the liquid outlet 112 are respectively positioned at both ends of the longest liquid path of the heating portion 100, so that the liquid flowing through the heating portion 100 is more sufficiently heated.

The liquid constant temperature heating apparatus according to the embodiments of the present disclosure can implement constant temperature heating of the liquid so as to supplement the liquid to the patient or prepare the solution with the temperature requirement.

Figure 2:
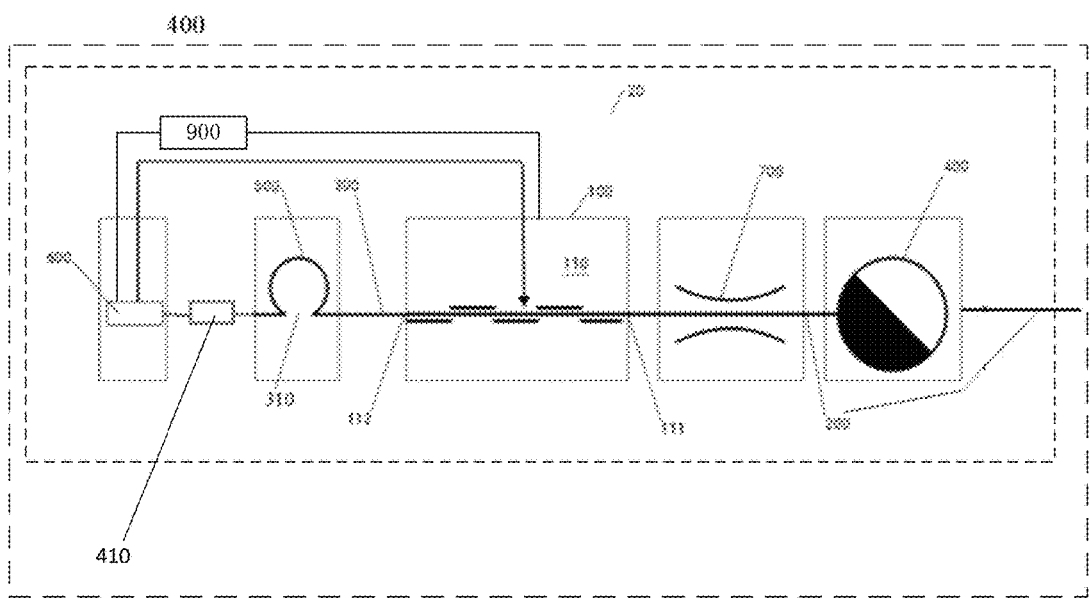
FIG. 2 is a schematic diagram of an infusion device according to an embodiment of the present disclosure.

An infusion device 400 according to an embodiment of the present disclosure will be described below in connection with FIG. 2.

The infusion device 400 according to the embodiments of the present disclosure includes a liquid constant temperature heating apparatus 20 and a cutoff catheter 410.

The cutoff catheter 410 is connected with a liquid outlet pipe 300 and communicated with a temperature sensor 600, and the cutoff catheter 410, in response to the detection result of the temperature sensor, selects whether to cut off flowing liquid or keep the liquid flowing.

For example, when the temperature sensor 600 detects out a temperature rise abnormality, the cutoff catheter 410 immediately cuts off the liquid flowing through the cutoff catheter 410 so as to avoid causing discomfort when the liquid which is abnormal in temperature rise is injected into a human body.

The infusion device according to the embodiments of the present disclosure, by utilizing the liquid constant temperature heating apparatus 20 according to the above-mentioned embodiments of the present disclosure, can provide injection suitable for the human body so as to avoid the case where discomfort occurs to affect the condition of the patient.

The infusion device according to the embodiments of the present disclosure, by utilizing the liquid constant temperature heating apparatus according to the above-mentioned embodiments of the present disclosure, can provide the injection suitable for the human body so as to avoid the case where discomfort occurs to affect the condition of the patient.

A formula milk preparation device 1 according to an embodiment of the present disclosure will be described below in connection with the drawing.

Figure 3:
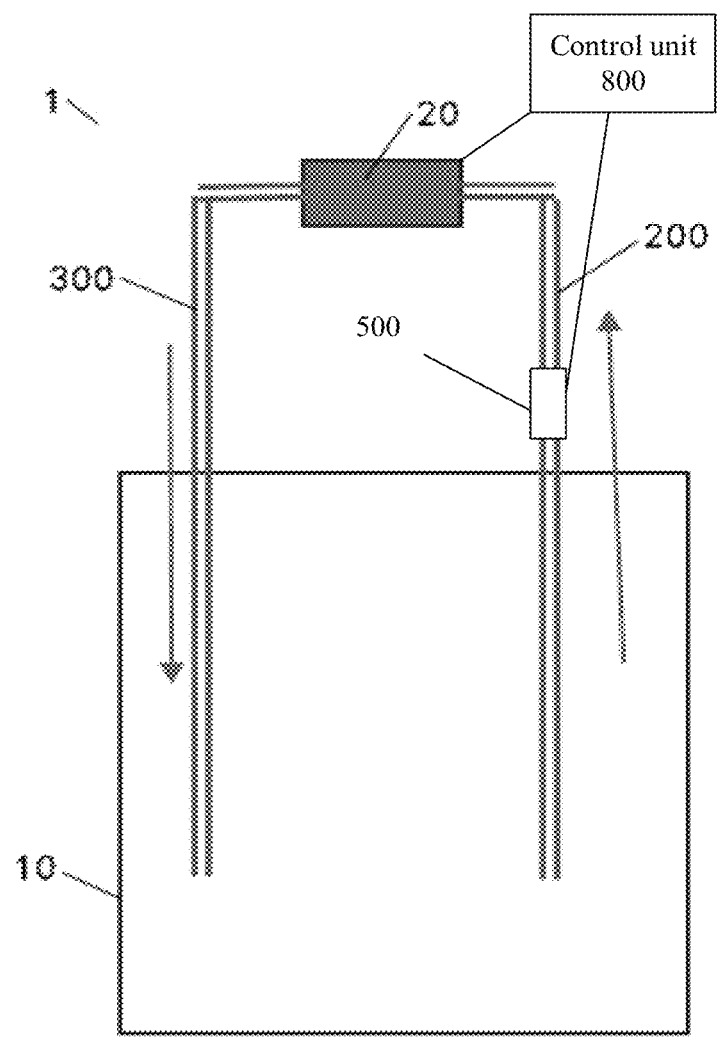
FIG. 3 is a formula milk preparation device according to an embodiment of the present disclosure.

As shown in FIG. 3, the formula milk preparation device 1 according to the embodiment of the present disclosure includes a storage container 10, an auxiliary temperature sensor 500 and a control unit 800. The formula milk preparation device 1 can be used for preparing formula milk for an infant in the NICU.

One end of a liquid inlet pipe 200, which faces away from a heating portion 100, and one end of a liquid outlet pipe 300, which faces away from the heating portion 100, extend into the storage container 10. The auxiliary temperature sensor is arranged on the liquid inlet pipe 200. The control unit 800 is in communication with a temperature sensor 600 and the auxiliary temperature sensor 500; when the difference between detection values of the temperature sensor 600 and the auxiliary temperature sensor is smaller than a preset threshold, at the moment, the liquid temperature accords with the requirement and information representing that the temperature meets the requirement is presented, or it is determined that the temperature does not accord with the requirement.

Exemplarily, the control unit can provide the information representing that the temperature meets the requirement to a user in various modes, for example, the control unit can display the information by a display screen, display the information in a way of lighting up a green light, can prompt the information by unique sound, or the like, and correspondingly, when it is determined that the temperature does not accord with the requirement, the information can be correspondingly displayed by the display screen, the information can be presented in a way of lighting up a red light, the information can be prompted by unique sound, or the like. The embodiments of the present disclosure does not make any limit thereto.

Exemplarily, the auxiliary temperature sensor 500 can be arranged at any position of the liquid inlet pipe 200, and the embodiments of the present disclosure does not make any limit thereto.

The formula milk preparation device 1 adopts a cyclic heating mode, the liquid inlet pipe 200 extracts liquid from the storage container 10 to the heating portion 100 to carry out heating, the heated liquid is returned to the storage container 10 from the liquid outlet pipe 300. The liquid inlet temperature is detected by utilizing the auxiliary temperature sensor, and a liquid outlet temperature is detected by utilizing the temperature sensor 600. When the temperature difference of the liquid inlet temperature and the liquid outlet temperature is smaller than a preset threshold, it is determined that the temperature of the liquid accords with the requirement and the liquid can be supplied to the infant. When the temperature difference of the liquid inlet temperature and the liquid outlet temperature is greater than or equal to the preset threshold, it is determined that the temperature of the liquid does not accord with the requirement and the liquid cannot be supplied to the infant.

The formula milk preparation device 1 according to the embodiments of the present disclosure utilizes the liquid constant temperature heating apparatus 20 according to the above-mentioned embodiments of the present disclosure, so that the overall temperature rise of the liquid is relatively fast and the case of local overheating cannot occur; and the formula milk preparation device 1 does not require a stirrer to carry out stirring for the liquid, so that the possibility that the liquid is polluted is reduced.

The formula milk preparation device according to the embodiments of the present disclosure, by utilizing the liquid constant temperature heating apparatus according to the above-mentioned embodiments of the present disclosure, is uniform in heating temperature and does not need to stir, so that the risk of pollution is reduced.

In the description to the present disclosure, the expression "an embodiment", "embodiments", "exemplary embodiment", "example", "specific example" or "examples" and so on are intended to present that the particular feature, structure, material or characteristics described in connection with these embodiments or examples should be included in at least one embodiment or example of the present disclosure. In the present disclosure, the exemplary description to the above mentioned expressions are not necessarily related to the same embodiment or example. Further, the particular feature, structure, material or characteristics that are described can be combined in any suitable ways in any one or more embodiments or examples.

Although the embodiments of the present disclosure have illustrate and describe the embodiments of the present disclosure, those skilled in the related art can understand that without departing from the spirit and principle of the present disclosure, these embodiments can be modified, amended or varied, and the scope of the present disclosure should be defined by those claims and their equivalents.

The application claims priority to the Chinese patent application No. 201710607279.3, filed on Jul. 24, 2017, the entire disclosure of which is incorporated herein by reference as part of the present application.

What is claimed is:

1. A liquid constant temperature heating apparatus, comprising:
   a heating portion, the heating portion having a heating chamber, and the heating chamber having a liquid inlet and a liquid outlet;
   a liquid inlet pipe, the liquid inlet pipe being connected with the liquid inlet of the heating portion;
   a liquid outlet pipe, the liquid outlet pipe being connected with the liquid outlet of the heating portion;
   a temperature sensor, the temperature sensor being arranged on the liquid outlet pipe and in communication with the heating portion;
   a controller, which is in signal connection with the temperature sensor by a signal and configured to control heating of the heating portion according to a measurement result of the temperature sensor; and
   a buffer, the buffer being arranged on the liquid outlet pipe,
   wherein the buffer is a telescopic pipe, the liquid outlet pipe has a gap, and two ends of the telescopic pipe are respectively connected with two ends of the gap of the liquid outlet pipe.

2. The liquid constant temperature heating apparatus according to claim 1, further comprising:
   a flow restriction valve, the flow restriction valve being arranged on the liquid inlet pipe.

3. The liquid constant temperature heating apparatus according to claim 2, further comprising:
   a check valve, the check valve being arranged on the liquid inlet pipe and unidirectionally conducted along a direction of the liquid inlet pipe, which faces the liquid inlet.

4. The liquid constant temperature heating apparatus according to claim 3, wherein the flow restriction valve is positioned between the check valve and the liquid inlet of the heating portion in a length direction of the liquid inlet pipe.

5. The liquid constant temperature heating apparatus according to claim 2, further comprising:
   a check valve, the check valve being arranged on the liquid inlet pipe and unidirectionally conducted along a direction of the liquid inlet pipe, which faces the liquid inlet.

6. The liquid constant temperature heating apparatus according to claim 2, wherein the controller is a Proportional-Integral-Derivative controller and is configured to acquire a temperature measurement time sequence of the temperature sensor and a signal, which corresponds to the time sequence and is input to the heating portion by the controller and generate a control parameter of the Proportional-Integral-Derivative controller by a neural network, and the neural network is a Long Short Term Memory network.

7. The liquid constant temperature heating apparatus according to claim 1, wherein a length of the telescopic pipe along a liquid flowing direction is greater than a distance between the two ends of the gap of the liquid outlet pipe.

8. The liquid constant temperature heating apparatus according to claim 1, wherein the check valve is positioned at the upstream of the heating portion along the liquid flowing direction.

9. The liquid constant temperature heating apparatus according to claim 1, wherein the temperature sensor is positioned at the downstream of the heating portion along the liquid flowing direction.

10. The liquid constant temperature heating apparatus according to claim 1, wherein the liquid inlet and the liquid outlet are respectively positioned at both ends of the longest liquid path of the heating portion.

11. The liquid constant temperature heating apparatus according to claim 1, wherein the controller is a Proportional-Integral-Derivative controller and is configured to acquire a temperature measurement time sequence of the temperature sensor and a signal, which corresponds to the time sequence and is input to the heating portion by the controller and generate a control parameter of the Proportional-Integral-Derivative controller by a neural network, and the neural network is a Long Short Term Memory network.

12. An infusion device, comprising:
- the liquid constant temperature heating apparatus according to claim 1; and
- a catheter, the catheter being connected with the liquid outlet pipe and in communication with the temperature sensor, and the catheter, in response to a detection result of the temperature sensor, cutting off flowing liquid or keeping the liquid flowing.

13. A formula milk preparation device, comprising:
- a storage container;
- the liquid constant temperature heating apparatus according to claim 1, one end of the liquid inlet pipe, which faces away from the heating portion, and one end of the liquid outlet pipe, which faces away from the heating portion, extending into the storage container.

14. The formula milk preparation device according to claim 13, further comprising:
- an auxiliary temperature sensor, the auxiliary temperature sensor being arranged on the liquid inlet pipe; and
- a control unit, the control unit being in communication with the temperature sensor and the auxiliary temperature sensor and when a difference between detection values of the temperature sensor and the auxiliary temperature sensor is smaller than a preset threshold, providing information representing that a temperature meets the requirement.

15. The liquid constant temperature heating apparatus according to claim 1, further comprising:
- a flow restriction valve, the flow restriction valve being arranged on the liquid inlet pipe.

16. The liquid constant temperature heating apparatus according to claim 15, wherein the flow restriction valve is positioned between a check valve and the liquid inlet of the heating portion in a length direction of the liquid inlet pipe.

17. The liquid constant temperature heating apparatus according to claim 1, further comprising:
- a check valve, the check valve being arranged on the liquid inlet pipe and unidirectionally conducted along a direction of the liquid inlet pipe, which faces the liquid inlet.

18. The liquid constant temperature heating apparatus according to claim 1, wherein the controller is a Proportional-Integral-Derivative controller and is configured to acquire a temperature measurement time sequence of the temperature sensor and a signal, which corresponds to the time sequence and is input to the heating portion by the controller and generate a control parameter of the Proportional-Integral-Derivative controller by a neural network, and the neural network is a Long Short Term Memory network.

* * * * *